United States Patent [19]

Orentreich et al.

[11] Patent Number: 4,758,234

[45] Date of Patent: * Jul. 19, 1988

[54] HIGH VISCOSITY FLUID DELIVERY SYSTEM

[75] Inventors: Norman Orentreich, 140 E. 72nd St., New York, N.Y. 10021; Joseph H. Vogelman, Roslyn, N.Y.

[73] Assignee: Norman Orentreich, New York, N.Y.

[*] Notice: The portion of the term of this patent subsequent to May 12, 2004 has been disclaimed.

[21] Appl. No.: 27,293

[22] Filed: Mar. 17, 1987

Related U.S. Application Data

[63] Continuation-in-part of Ser. No. 841,971, Mar. 20, 1986, Pat. No. 4,664,655.

[51] Int. Cl.$^4$ ............................................. A61M 5/245
[52] U.S. Cl. ................................................. 604/232
[58] Field of Search ............... 604/232, 218, 211, 208, 604/407, 416

[56] References Cited

U.S. PATENT DOCUMENTS

| | | |
|---|---|---|
| Re. 27,645 | 5/1973 | Drummond et al. . |
| 605,386 | 6/1898 | Brown . |
| 637,405 | 11/1899 | Papendell . |
| 2,373,520 | 12/1944 | Wallin . |
| 2,561,233 | 3/1949 | Ryan et al. . |
| 2,607,342 | 8/1952 | Abel . |
| 2,627,857 | 2/1953 | Marcelli ............................. 604/407 |
| 2,735,735 | 2/1956 | Abel . |
| 2,761,447 | 9/1956 | Hersee . |
| 2,842,127 | 7/1958 | Everett . |
| 2,933,087 | 4/1960 | Hamilton . |
| 3,026,872 | 3/1962 | Prater, Jr. . |
| 3,110,309 | 11/1963 | Higgins . |
| 3,150,801 | 9/1964 | Hamilton . |
| 3,343,539 | 9/1967 | Moorhouse ......................... 604/211 |
| 3,366,113 | 1/1968 | Hobbs . |
| 3,537,453 | 11/1970 | Drummond et al. ................ 604/232 |
| 3,556,099 | 1/1971 | Knight et al. ....................... 604/232 |
| 3,566,859 | 3/1971 | Schwartz . |
| 3,730,389 | 5/1973 | Harris, Sr. . |
| 3,735,900 | 5/1973 | Gores .................................. 604/416 |
| 3,809,298 | 5/1974 | Harris, Sr. et al. . |
| 3,828,987 | 8/1974 | Drummond et al. . |
| 3,848,593 | 11/1974 | Baldwin ........................... 604/232 X |
| 3,873,274 | 3/1975 | Neisius ............................ 604/407 X |
| 3,923,207 | 12/1975 | Kyogoku . |
| 3,958,570 | 5/1976 | Vogelman et al. . |
| 4,143,428 | 3/1979 | Cohen . |
| 4,189,065 | 2/1980 | Herold . |
| 4,281,653 | 8/1981 | Barta et al. . |
| 4,333,456 | 6/1982 | Webb .................................. 604/232 |
| 4,404,862 | 7/1983 | Harris, Sr. et al. . |
| 4,475,905 | 10/1984 | Himmelstrup . |
| 4,664,655 | 5/1987 | Orentreich et al. ................ 604/232 |

Primary Examiner—John D. Yasko
Attorney, Agent, or Firm—Panitch Schwarze Jacobs and Nadel

[57] ABSTRACT

A carpule system for the microadministration of viscous fluid including a carpule syringe comprising a stainless steel delivery needle having an interior diameter in the range of from about 0.004 inches to about 0.007 inches and a generally cylindrical fluid containing carpule. The carpule has a bore with a cross-sectional area which is about 100 to 400 times greater than the cross-sectional area of the bore of the delivery needle and a movable plug sealing the fluid within the carpule. The needle is secured to one end of the carpule and a generally cylindrical housing member is adapted to receive the carpule, the housing member having means on one end for retaining the one end of the carpule. An adapter member is secured to the other end of the housing member to secure the other end of the carpule and adapter retention means are provided for securing the adapter member to the other end of the housing member. A plunger is adapted to actually displace the carpule plug within the carpule bore for delivery of the fluid through the needle. Gripper means are provided for facilitating movement of the plunger relative to the carpule.

15 Claims, 6 Drawing Sheets

4,758,234

HIGH VISCOSITY FLUID DELIVERY SYSTEM

BACKGROUND OF THE INVENTION

This is a continuation-in-part of U.S. Ser. No. 841,971 filed Mar. 20, 1986, now U.S. Pat. No. 4,664,655.

FIELD OF THE INVENTION

This invention relates to syringes. More specifically, this invention relates to syringes for the administration of small amounts of high viscosity fluids, and in particular, silicone fluid for dermatological purposes.

BRIEF DESCRIPTION OF THE PRIOR ART

Syringes adapted for the micro-administration of highly viscous liquids, such as silicone fluid, are known in the art. For example, U.S. Pat. No. 3,958,570 discloses hypodermic syringes and syringe capsules which maintain a high pressure between the syringe plunger and barrel. The syringes are constructed so that the interface between the syringe barrel and syringe plunger is resilient and of low friction and so that zero or negative clearance is maintained between the barrel and the plunger. Preferably, the syringe barrel is formed from a resilient plastic material such as polypropylene or polyethylene; and the syringe plunger is a rigid rod made of a high strength material such as steel or an engineering plastic such as polyoxymethylene (acetal) resin. The plunger rod is preferably coated with a low friction material, such as a fluorinated hydrocarbon resin, or a silicone resin, or any other similarly low friction, preferably resilient, material.

One difficulty encountered with syringes constructed using polypropylene barrels, such as disclosed in U.S. Pat. No. 3,628,523, is that such syringes are reusable only to a limited extent. In order to reuse syringes employed in medical procedures it is necessary to sterilize the syringes before each use. Syringes made using thermoplastic materials having relatively low glass transition temperatures, such as polypropylene, cannot be autoclaved for sterilization. Instead, they must be exposed to a sterilizing gas, such as ethylene oxide. However, even when this precaution is taken to guard against thermally deforming the polypropylene syringe, it has been found that syringes constructed using polypropylene barrels may be reused for only a limited number of times before cracks or leaks develop, or the syringes become otherwise unsuitable for further use.

Other types of prior art syringes employ various sealing techniques which are appropriate for low pressure applications, but which are inadequate for high pressure micro applications, in that the prior art barrels tend to crack and/or the syringes tend to develop leaks.

The present invention provides a remedy to the problem of limited life expectancy encountered with syringes having polypropylene barrels. The present invention provides syringes which may be reused a multitude of times and can be sterilized between uses by connventional techniques such as autoclavin.

SUMMARY OF THE INVENTION

Briefly stated, the present invention comprises a carpule system for the micro-administration of viscous fluids which includes a carpule syringe. The carpule syringe includes a stainless steel delivery needle and a generally cylindrical housing member having openings at each end and adapted to receive a fluid-containing carpule, the housing member includes means for retaining one end of the carpule. The carpule has an interior bore with an interior cross sectional area which is from about 100 to 400 times greater than the cross-sectional area of the bore of the delivery needle. The carpule is provided with a movable plug sealing the fluid within the carpule. The needle is secured to the one end of the carpule. An adapter member and carpule spring are provided to secure the carpule within the housing member. The carpule syringe also includes adapter retention means to secure the adapter to the end of the housing member, a plunger adapted to axially displace the plug within the carpule bore for delivery of the fluid, and gripper means to facilitate movement of the plunger with respect to the carpule.

DESCRIPTION OF THE DRAWINGS

For the purpose of illustrating the invention there is shown in the drawings forms which are presently preferred; it being understood, however, that the invention is not limited to the precise arrangements and instrumentalities shown.

DETAILED DESCRIPTION OF THE PREFERRED EMBODIMENTS

Figure 1:
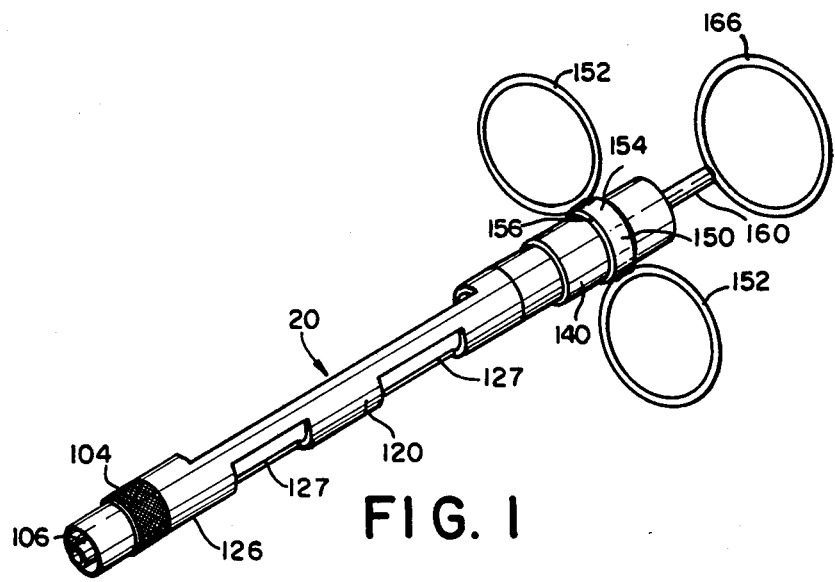
FIG. 1 is a perspective view of a presently preferred embodiment of a syringe without the delivery needle which is to be directly filled in accordance with the present invention.
Figure 2:
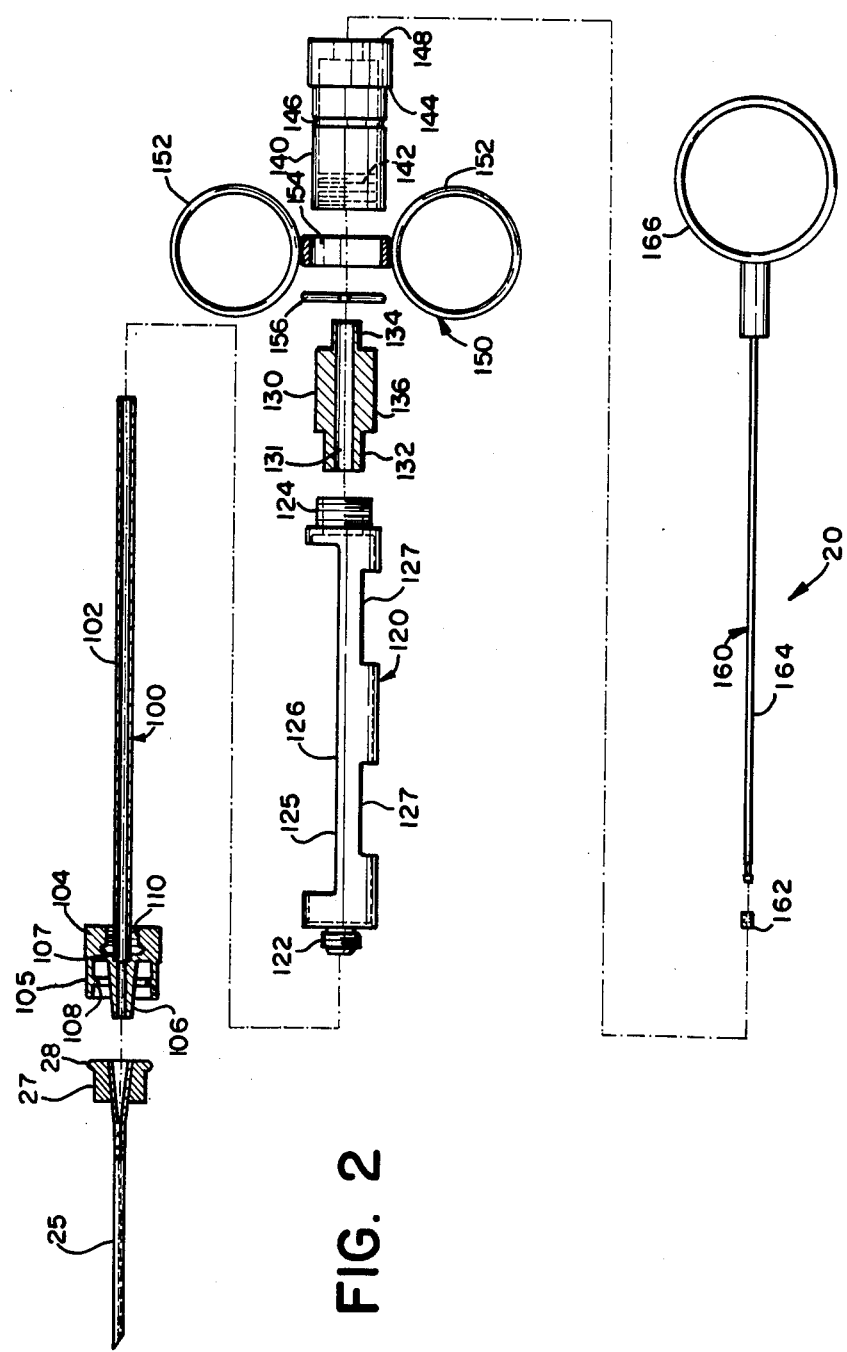
FIG. 2 is an exploded partially sectioned side elevational view of the syringe illustrated in FIG. 1 with the delivery needle.

Referring now to the drawings, in which like reference numerals identify like elements throughout the several views, there is shown in FIG. 1 a perspective view and in FIG. 2 an exploded partially sectioned side elevational view of a preferred embodiment of a syringe 20 according to the present invention. The syringe 20 is adapted for being directly filled from a reservoir of viscous fluid (not shown in FIGS. 1 and 2).

In this application, the term "proximal," when used in reference to an element of a syringe or carpule, refers to the forward end (left end when viewing FIGS. 1, 2, 4, 5a and 5b) thereof which is proximate the delivery needle. Similarly, the term "distal," when used herein in reference to an element of a syringe or carpule refers to the rearward end (right end when viewing FIGS. 1, 2, 4, 5a and 5b) thereof which is situated away from the delivery needle. Unless otherwise indicated, all of the components of the syringes of the present invention are preferably made from stainless steel or some other material having similar properties.

Referring now to FIG. 2, which is an exploded partially sectioned side elevational view of a syringe 20, there is illustrated a presently preferred direct fill syringe 20 according to the present invention. The syringe 20 is comprised of a special extra thick flanged generally tubular delivery needle 25 of a type well known in the art and having a luer-type female connector 27 with a flange 28 on the distal end. The delivery needle 25 is beveled on the proximal end and is non-coring. The luer-type connector 27 is adapted for attachment to a barrel assembly shown generally as 100.

The size of the needle chosen for use with syringes of the present invention depends on the dermatological application for which the syringe is used. For example, when silicone fluid is to be inserted behind a fine line in the skin, a needle having a small diameter, such as a 30 gauge needle, is preferred for accuracy. A relatively large hydraulic force is required to make the relatively viscous silicone fluid flow through the bore of a needle having a small diameter. The necessary force is obtained by use of a syringe having a bore with a cross-sectional area substantially greater than the corresponding area of the delivery needle. In human dermatological applications it has been found that delivery needles having an interior diameter from about 0.004 inches to 0.007 inches are most frequently useful. Other applications may require needles having different interior diameters.

In order to apply sufficient force on the viscous fluid, which for dermatological application typically is a silicone fluid having a viscosity ranging from about 150 to 350 centistokes, it is preferred that the bore of the syringe have a cross-sectional area about 100 to 400 times greater than the cross-sectional area of the delivery needle. Syringes which are intended for use with fine needles and viscous silicone fluids for human dermatological use typically have a capacity on the order of 0.5 ml.

The barrel assembly 100 is comprised of barrel 102 which is formed of a predetermined length of precision diameter stainless steel needle tubing having an inside cross-sectional area which is from about 100 to 400 times greater than the cross-sectional area of the bore of delivery needle 25. One end of the barrel 102 is secured to a connector component 104.

Connector component 104 has a male luer connector or a luer cone 106 and a surrounding sheath 105 having internal threads 108. The luer cone 106 is adapted to mate with the female luer-type connector 27 on the delivery needle 25 to form a secure, pressure-tight seal in a manner well known in the art. The connector component 104 has an inner axial bore 107 which is adapted to receive the proximal end of a barrel 102 such that the barrel 102 may be press fit into the inner axial bore 107. Alternatively, the proximal end of the barrel 102 may be permanently attached to the inner axial bore 107 by, for example, welding, soldering, or the like. Whatever the means of attachment used, whether it be by press fitting which allows for replacement of damaged barrels and the like, or whether it be by permanent means, the mode of attachment must be such that a pressure-tight seal is formed between the barrel 102 and the connector component 104. Thus, the connector component 104 constitutes means for attaching the barrel 102 to the needle 25 and the axial bore 107 provides fluid communication between the barrel 102 and the needle 25.

In addition to the inner axial bore 107 adapted to receive the barrel 102, the distal end of the connector component 104 has an axial receiving bore 110 which has a larger interior diameter than the exterior diameter of the barrel 102. The receiving bore 110 is threaded as shown.

A generally cylindrical housing member or housing 120 has an opening at each axial end and means on one end for attachment of the housing 120 to the barrel assembly 100. In the embodiment illustrated in FIG. 2, the attachment means comprises the threads on the exterior of the proximal end 122 of the housing 120. As illustrated in FIG. 2, the generally cylindrical proximal end 122 of the housing 120 has a reduced diameter in comparison with the diameter of the body 126 of the housing 120. The threads on the proximal end 122 of the housing 120 are adapted to engage the interior threads of the axial bore 110 of the connector component 104 to secure the housing 120 to the barrel assembly 100. The distal end 124 of the housing 120 also has exterior threads. Sections of the housing 120 may be cut away or may be left open as illustrated in FIGS. 1 and 2, to provide openings 125, 127 to permit easy visual inspection of the syringe components and to facilitate assembly.

A generally cylindrical adapter member or adapter 130 has an axial bore 131 which is adapted to snugly receive the distal end of the barrel 102 to provide support for the distal end of the barrel 102. For example, when the exterior diameter of the barrel 102 is 0.110 inches (0.279 cm), the axial bore 131 has a diameter of 0.112 inches (0.284 cm). The adapter 130 may be made of brass, or another metal, or the like. Although the axial bore 131 of the adapter 130 contains the barrel 102, and the adapter 130 supports the barrel 102 against lateral movement, the barrel 102 is not rigidly affixed to the adapter 130. The generally cylindrical proximal end 132 of the adapter 130 fits within the opening at the distal end 124 of the housing 120. The generally cylindrical distal end 134 of adapter 130 has a diameter smaller than either the proximal end 132 of the adapter 130, or the central section 136 of adapter 130.

An adapter retention means, in the present embodiment a generally cylindrical cap 140, is provided for securing the adapter 130 to the distal end of the housing 120. The cap 140 has an interior bore 142 having a diameter larger than the greatest exterior diameter of the adapter 130. The proximal end of the interior bore 142 is threaded to mate with the external threads on the distal end 124 of the housing 120. The depth of the interior bore 142 is sufficient so that the cap 140 may be placed over the adapter 130 and threaded onto the housing 120 so that the distal end 134 of the adapter 130 fits snugly against the distal wall 148 of the cap 140, thus securing the adapter 130 to the distal end 124 of the housing 120. The exterior surface of cap 140 is provided with a generally annular shoulder 144 and a generally annular groove 146.

The syringe includes gripper means, in the presently preferred embodiment including finger grip means or finger grip 150. The finger grip 150 comprises a pair of finger loops 152 each of which are connected to a cylindrical grip mount 154. The loops 152 lie generally in the same plane. Although loops are preferred, other grip geometries, such as semicircles and straight tabs, adapted to firmly engage the index and middle fingers of the user of the syringe, may also be used. The interior diameter of the grip mount 154 is substantially the same as the diameter of the exterior surface of the cap 140 and the distal end of the grip mount 154 abuts the annular shoulder 144. A generally annular spring clip 156 is provided to fasten the finger grip 150 in place around the cap 140 by pressing the grip mount 154 against the annular shoulder 144.

A plunger 160 is positioned within the axial opening in the distal end 148 of the cap 140, and within the barrel 102. The plunger 160 includes a generally cylindrical plunger tip 162 made from polytetrafluorethylene (available from Hamilton Co. of Reno, Nev. as part number 13409), and an elongated plunger rod 164, on which is mounted thumb grip means, in the present embodiment a thumb ring 166. The thumb ring 166 may be replaced with parts having other geometries which are adapted to firmly engage the thumb of the syringe user. The plunger tip 162 may be made of any elastic solid which is chemically inert with respect to the viscous fluid to be delivered by the syringe. The plunger tip 162 is friction fit on the end of the plunger 160 and is adapted to seal the viscous fluid within the barrel 102. Accordingly, the outer diameter of the plunger tip 162 is at least slightly greater than the interior diameter of the barrel 102.

The presently preferred direct fill syringe 20 shown in FIGS. 1 and 2 is assembled as shown in FIG. 2 by first threading the generally cylindrical housing 120 onto the proximal end of the barrel assembly 100 such that the threads on the exterior of the proximal end 122 of the housing 120 engage the mating threads on the interior surface of the receiving bore 110 in the connector component 104.

After the barrel assembly 100 and the housing 120 have been connected together, the adapter 130 is placed over the barrel 102 so that the proximal end 134 of the adapater 130 lies within the distal end 124 of the housing 120.

Next, the grip mount 154 of the finger grip 150 is placed over the cap 140 abutting the annular shoulder 144. The spring clip 156 is then placed into the annular groove 146 on the cap 140, pressing against the grip mount 154 to retain the finger grip 150 on the cap 140. Alternatively, the finger grip 150 may be mounted on the cap 140 after the cap 140 is threaded onto the housing 120. The finger grip 150 may also be mounted on the cap 140 to form a subassembly prior to beginning assembly of the remainder of the syringe 20.

The cap 140 is then placed over the adapter 130 and threaded onto the housing 120 until the distal end 132 of the adapter 130 fits snugly against the distal wall 148 of the cap 140.

The plunger tip 162 is secured to the end of the plunger rod 164. The plunger 160 fitted with the plunger tip 162 is inserted through the hole in the distal wall 148 of the cap 140 and into the barrel 100 of the syringe 20. The plunger 160 may be preassembled.

In the direct fill syringe 20 the barrel 102 is supported proximate each end to prevent mechanical deformation of the barrel during syringe use. The barrel is rigidly affixed to the remainder of the syringe proximate its proximal end and supported against lateral deflection proximate its distal end.

The assembled syringe 20 may be sterilized by any means known in the art, such as by autoclaving, by immersion in a sterilizing fluid such as ethylene oxide, or the like. Subsequently, the syringe may be filled with fluid as follows.

Figure 3:
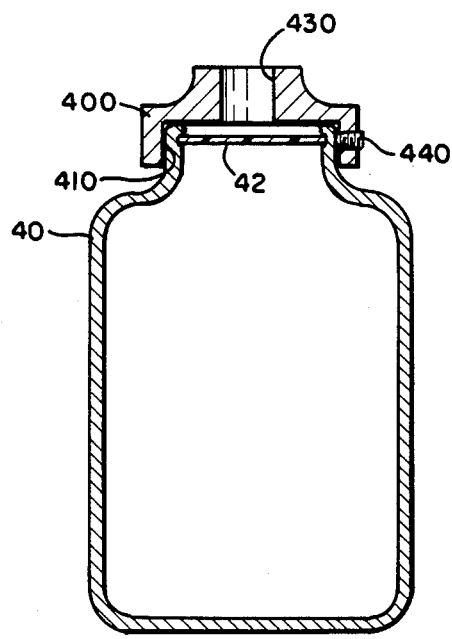
FIG. 3 is a cross-sectional side elevational view of a viscous fluid container fitted with an adapter for use in filling the syringe of FIG. 1.

A bottle adapter 400, illustrated in FIG. 3, is mounted on a container such as a bottle 40 having a gasket seal 42 and capped with a 20 millimeter diameter cap (not illustrated), and containing the fluid to be delivered, such as silicone fluid. The bottle adapter 400 has a bottle receiving internal cavity or bore 410 adapted to fit over the mouth of the bottle 40. The bottle adapter 400 is secured on the bottle 40 by suitable means, for example, a plurality of spaced set screws 440 (only one shown in FIG. 2). A one-half inch (1.26 cm) long, No. 16 non-coring needle (not illustrated), with a luer taper hub, but without a luer lock, is placed into the bottle adapter 400 such that the needle penetrates through the polytetrafluorethylene gasket seal 420. The syringe 20 is filled by inserting the luer taper 106 of the assembled syringe 20 into the matching taper of the No. 16 needle. The bottle 40 and the syringe 20 are inverted and the plunger 160 is pushed inwardly (toward the proximal end of the syringe) to expel air from the barrel 102. The plunger 160 is then slowly withdrawn about three-quarters of its length to draw the fluid through the needle and into the barrel 102 to fill the syringe 20. The syringe 20 is then withdrawn from the No. 16 needle and the 30 gauge delivery needle 25 is attached to the syringe 20.

In the assembled direct fill syringe 20 illustrated in FIG. 1, the high viscosity fluid is contained within the barrel 102 until the fluid is to be administered to a patient. Because the interior cross-sectional area of the barrel 102 is from about 100 to 400 times greater than the cross-sectional area of the bore of the delivery needle, a high viscosity fluid, for example, a silicone fluid having a viscosity in the range of from about 50 centistokes to 2000 centistokes, can be easily and controllably administered.

Figure 4:
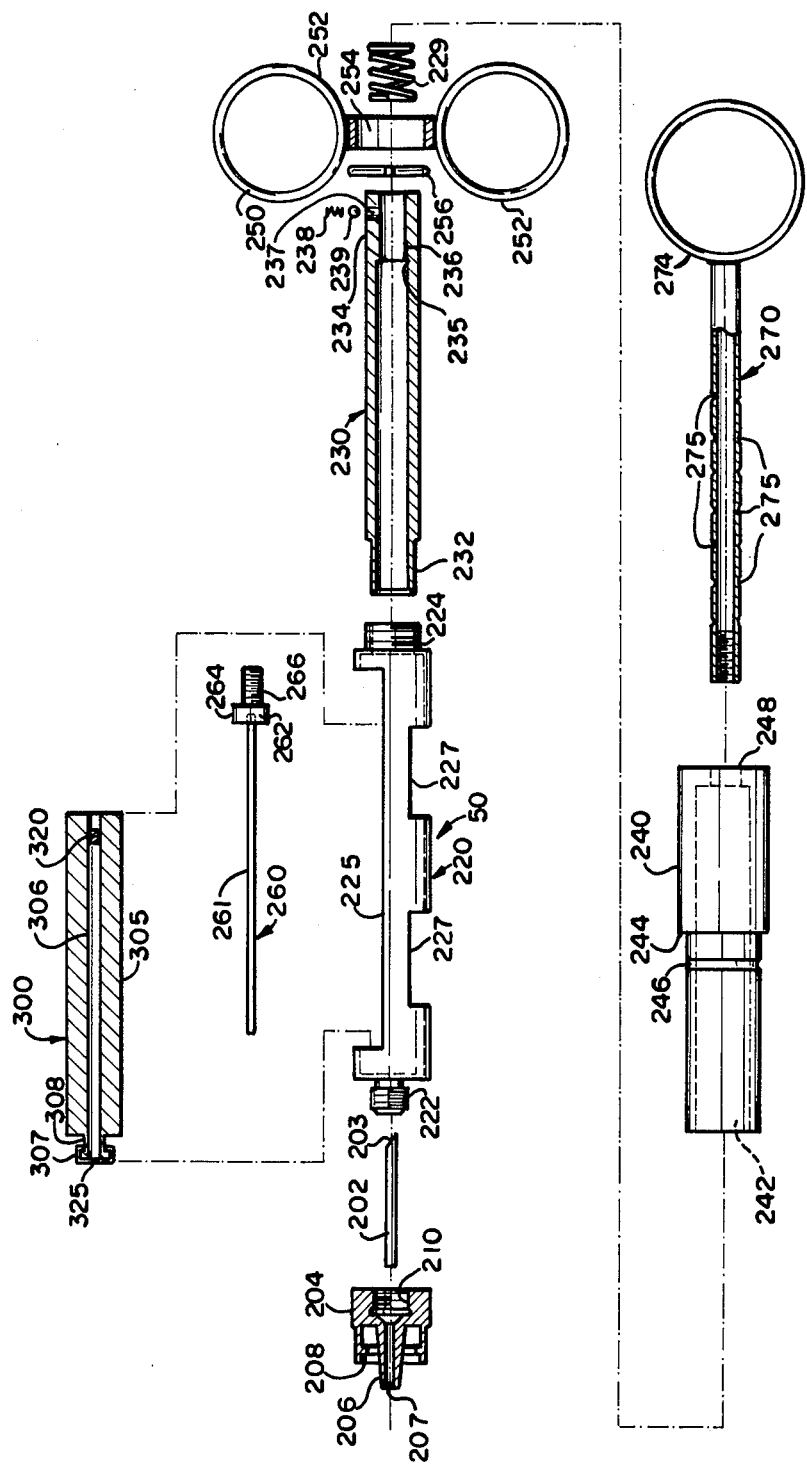
FIG. 4 is an exploded partially sectioned side elevational view of a second preferred embodiment of a syringe in accordance with the present invention adapted for use with carpules containing viscous fluid and a carpule for use with the syringe.

In a second preferred embodiment, illustrated in FIG. 4, the present invention provides a carpule delivery system adapted for injecting high viscosity fluid contained within prepackaged carpules. The carpule syringe shown generally as 50 of the second illustrated embodiment includes the special extra thick flanged luer-locking 30 gauge delivery needle (not shown in FIG. 4). The needle has a luer-type connector component (not shown in FIG. 4) on the distal end and being beveled on its proximal end to provide a non-coring needle of the type described above in connection with respect to FIGS. 1 and 2.

The connector component 204 is similar to the connector component 104 of the direct fill syringe 20 illustrated in FIGS. 1 and 2. The delivery needle may be attached to the carpule syringe 50 in the same manner as described above by engaging the male luer cone 206 of the connector component 204 with the female luer connector (not shown) on the needle. Similarly, the receiving bore 210 of the connector component 204 is threaded to receive the exterior threads on the proximal end 222 of the housing 220. The inner axial bore 207 of the connector component 204 is adapted to snugly receive one end of a tubular member or tube 202 by a friction fit. In contrast to the direct fill syringe 20, the tube 202 is relatively short in comparison with barrel 102 and has a distal end which is beveled to provide a non-coring needle tip 203. The needle tip 203 provides a means for puncturing the seal of carpules which are inserted into the carpule syringe 50.

In an alternative embodiment (not illustrated), instead of a luer-locking needle 25 and a separate needle-tipped tube 202, connector component 204 may be fit with a double-tipped needle which is press fit into inner axial bore 207 to extend outwardly from the connector component 204 in both axial directions.

The generally cylindrical housing 220 of the carpule syringe 50 may be identical to, and is preferably interchangeable with, the housing 120 of the direct fill syringe 20 illustrated in FIGS. 1 and 2. The housing 220 has a proximal end 222 which has a reduced diameter in comparison with the diameter of the body 226 of the housing 220. The proximal end 222 of the housing 220 has an axial opening through which the tube 202 may pass. The proximal end 222 of the housing 220 has exterior threads which are adapted to engage with the interior threads on the receiving bore 210 of the connector component 204 to secure the connector component 204 and the delivery needle (not shown) to the housing 220. The distal end 224 of housing 220 also has exterior threads which are adapted to engage interior threads on the interior bore 242 of a cap 240.

The housing 220 has a large elongated medial opening 225 of sufficient length and depth so that a carpule may be inserted through the opening 225 into the assembled syringe 50. Small medial openings 227 in the housing 220 facilitate insertion and removal of carpules.

The carpule 300 illustrated in FIG. 4 contains the high viscosity fluid, in the present embodiment silicone fluid, to be delivered by the carpule syringe 50. The carpule 300 has a carpule body 305 manufactured from a solid, generally rigid material such as glass, or stainless steel or the like. The interior bore 306 of the carpule 305 has a cross-sectional area which is about 100 to 400 times greater than the cross-sectional area of the bore of the delivery needle (not illustrated). The interior bore 306 containing the silicone fluid is sealed at its distal end by a movable generally disc-like plug or insert 320. The insert 320 is manufactured from polytetrafluorethylene or another similar elastic solid which is chemically inert with respect to the fluid contained within the carpule 300. The insert 320 has a slightly greater diameter than the diameter of the interior bore 306 to provide a tight sealing fit. The proximal end of the carpule 300 has an annular collar 307 and an annular groove 308 which are substantially identical to the standard dental cartridge. Accordingly, a standard polytetrafluoroethylene dental cartridge cap may be employed as a tightly fitting carpule cap 325 to seal the proximal end of the carpule 300.

Means are provided to urge and maintain the carpule 300 into abutting engagement with the proximal end of the housing 220. In the present embodiment the means comprises a coil carpule spring 229, preferably manufactured from spring steel, and having an exterior diameter less than the diameter of the bore of the cap 240. The carpule spring 229 exerts sufficient force when compressed as described below so that carpule 300 is held tightly within the housing 220.

A generally cylindrical adapter member or adapter 230 having a first or large axial bore 231 of sufficiently large inside diameter to permit the plunger rod assembly 260 to pass therethrough is provided. The proximal end 232 of the adapter 230 has a reduced outer diameter and a beveled end 233 to engage and retain the carpule 300 within the housing 220 when the carpule syringe 50 is assembled. Proximate the distal end 234 of the adapter 230, the adapter 230 has a second or small axial with a bore 236 reduced cross-sectional area. A shoulder 235 is formed between the sections of the bore having different interior diameters. As discussed below, the shoulder 235 serves to limit the withdrawal of the plunger rod assembly 260 from the syringe when the syringe is loaded with a carpule.

The distal end 234 of the adapter 230 includes detent means, in the present embodiment, a detent hole 237 extending generally perpendicular to the axis and a detent ball 239 partially protruding into the bore 231 of the adapter 230. A detent spring 238 is provided to urge the detent ball 239 towards the bore 231.

The generally cylindrical cap 240 also has an interior bore 242 which is greater in diameter than the largest exterior diameter of adapter 230 and which is adapted to receive the carpule spring 229 and the adapter 230. The proximal end of interior bore 242 is threaded to engage the exterior threads on the distal end 224 of housing 220 to hold the adapter 230 and cap 240 in place. The exterior surface of cap 240 is provided with a generally annular shoulder 244 and a generally annular groove 246.

Corresponding to the finger grip 150 of the above-described direct fill syringe 20, the finger grip 250 comprises finger loops 252 connected to a generally cylindrical grip mount 254. The interior radius of the grip mount 254 is substantially the same as the radius of the exterior surface of the cylindrical cap 240 such that the grip mount 254 is adapted to receive the exterior surface of the cylindrical cap 240. A generally annular spring clip 256, preferably manufactured from spring steel, is adapted to be received in annular groove 246. The spring clip 256 is adapted to press the grip mount 254 against the annular shoulder 244 to hold the finger grip 250 on cap 240. As in the case of the direct fill syringe 20, other finger grip geometries may be used. As in the direct fill syringe 20, the finger grip 250 and cap 240 may be preassembled.

The syringe plunger includes a plunger rod assembly 260 and a plunger extension 270. The plunger rod assembly 260 comprises a plunger rod 261, having a diameter slightly less than the interior diameter of the carpule bore 308, and a plunger adapter 262. The distal end of the plunger rod 260 is threaded to engage interior threads on the proximal end of the plunger adapter 262 when the syringe is assembled. The plunger adapter 262 includes a hexagonal head 264 having a diameter less then the diameter of the large diameter bore 231 of the adapter 230, but greater than the diameter of the small diameter bore 236 of the adapter 230.

The generally tubular plunger extension 270 may be inserted through the hole in wall 248 into the cap 240. The distal end 266 of the plunger adapter 262 has exterior threads which are adapted to engage threads on the distal end of the plunger extension 270. The head 264 of the plunger road assembly 260 serves to prevent the plunger from being withdrawn from the syringe when the carpule 300 is loaded into the syringe. The plunger extension 270 is terminated at its distal end by a thumb grip means or thumb ring 274. As in the case of the direct fill syringe 20, instead of the thumb ring 274, parts having other geometries adapted to firmly engage the thumb of the syringe user may be employed.

Spaced, generally annular detent grooves 275 are located on the exterior surface of the plunger extension 270, preferably at a separation of 0.05 inches (0.14 cm). The grooves 275 are sequentially engaged by the spring loaded detent ball 239 as the plunger is moved inwardly through the carpule syringe 50. This action tactilely signals advance of the plunger to the individual administering fluid using the syringe.

Assembly of the carpule syringe 50 is begun by inserting the tube 202 into the inner axial bore 207 of the connector component 204 such that the needle tip 203 is oriented towards the distal end of the carpule syringe 50. The tube 262 and connector component 204 can be permanently joined and used as a subassembly. The proximal end 222 of the housing 220 is placed over the tube 202 and the housing 220 is threaded into the receiving bore 210 of the connector component 204.

The finger grip 250 is placed in position on the cap 240 against the annular shoulder 244 and the spring clip 256 is inserted into the annular groove 246 to hold the finger grip 250 in position. Alternatively, the finger grip 250 may be attached to the cap 240 after the cap 240 is threaded onto housing 220. Preferably, the finger grip 250, spring clip 256, and cap 240 form a subassembly.

The carpule spring 229 is inserted into the distal end 224 of the cap 240. The detent ball 239 is then inserted into the detent hole 237 of the adapter 230 so that the detent ball partially protrudes into the central bore of the adapter 230. The detent spring 238 is inserted into the detent hole 237 and is compressed while the adapter 230 is inserted into the interior bore 242 of the cap 240. The cap 240 containing the adapter 230, is threaded onto the distal end 224 of the housing 220.

The plunger is assembled by screwing together the plunger rod assembly 260 and the plunger extension 270 within the syringe 50. The plunger extension 270 is first inserted through the hole in the wall 248 of the cap 240. The plunger extension 270 is positioned in the syringe 50 so that it protrudes within the housing 220. The plunger assembly 260 is then inserted through the large medial opening 225 in the housing 220 and secured to the end of the plunger extension 270.

Next, the plunger is withdrawn until the outward travel of the plunger is stopped by the abutment of the hexagonal head 264 of the plunger adapter 262 against the shoulder 235 within the bore of the adapter 230. Further withdrawal of the plunger compresses the carpule syringe 229 positioned within the cap 240 between the adapter 230 and the end of the cap 240, permitting the distal end of the carpule 300 to enter the housing 220 through the large medial opening 225. A generally cylindrical carpule 300 is inserted into the housing 220. Release of the plunger causes the carpule spring 229 to urge the adapter 230 against carpule 330, thus securing the carpule 300 within the syringe 50. On insertion of the carpule 300 into the housing 220, the carpule cap 325 is pierced by the tip 203 of the tube 202.

Finally, a delivery needle 25 (not illustrated), such as discussed in relation to the first embodiment illustrated in FIGS. 1, 2 and 3 above, is affixed to connector component 204.

Figure 5A:
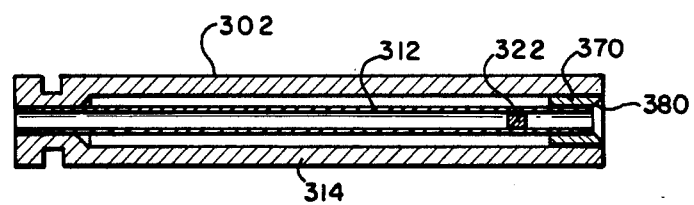
FIGS. 5a and 5b are sectional views of two additional types of carpules adapted for use with the syringe illustrated in FIG. 4.
Figure 5B:
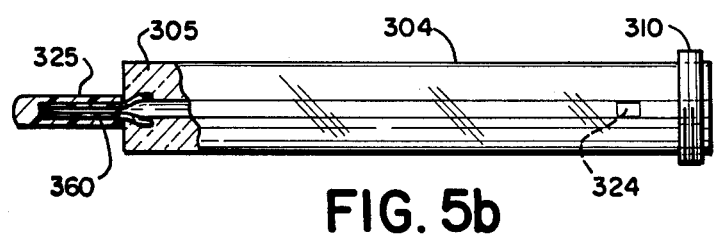

FIGS. 5a and 5b illustrates alternative carpules or cartridges which may be employed with the carpule syringe 50. The carpule 302 illustrated in FIG. 5a is similar in design to the carpule 300 illustrated in FIG. 4 except that a carpule tube 312, preferably manufactured from stainless steel tubing or a material with similar properties, contains the fluid to be delivered. The exterior housing 314 of the carpule 302 is preferably made of aluminum or a similar material. The carpule 302 is sealed at one end by a polytetrafluoroethylene cap (not illustrated) and at the other by a polytetrafluoroethylene plug 322. The carpule tube 312 is supported at its distal end by an aluminum ring 370 positioned within the interior bore at the distal end of the carpule housing 314. The interior bore of the ring 370 has a bevel 380 to facilitate insertion of the plunger rod 260.

The carpule 304 illustrated in FIG. 5b has a glass body 305 into which is sintered a carpule needle 360 which is covered with a soft silicone rubber or polytetrafluorethylene cap 325. The cap 325 has been added after filling and sterilization of the carpule 304. Carpule 304 is sealed at its distal end with an plug 324, and has a metal collar 310, having an exterior thread, which is secured to the exterior distal surface of the carpule 304. When this carpule 304 is used, the connector component 204 and the tube 202 are omitted from the carpule syringe 50. Instead, the carpule needle 330, which is about one inch (2.54 cm) long, protrudes through the central bore of the proximal end 222 of the housing 220 (not illustrated) and extends approximately one-half inch (1.27 cm) therebeyond. The threads of the rear collar 310 match those at the distal end 224 of the housing 220 and are engaged by the interior threads in the interior bore at the proximal end of the cap bore 242 when a carpule syringe 50 employing the carpule 304 is assembled.

In the carpule syringe 50, the fluid conduit between the carpule 300 and the delivery needle 25 comprises the tube 202 and the portion of the inner axial bore 207 of the connector component 204 extending between the tube 202 and the delivery needle 25. When the tube 202 and delivery needle 25 are replaced by a single double-tipped needle (not illustrated) extending from the carpule 300 through the interior-bore 207 of the connector component 204 as discussed above, the fluid conduit comprises the double-tipped needle. Similarly, when a carpule 304 having a glass body 305 into which is sintered a carpule needle 360, as illustrated in FIG. 5b, is used in the carpule syringe 50, the fluid conduit comprises the carpule needle 360.

Referring now to FIGS. 6, 7, 8 and 9, there is shown a third preferred embodiment of the present invention. The third preferred embodiment is, in many respects, exactly the same as the second preferred embodiment shown in FIG. 4 and described in detail above and the carpule is substantially the same as the carpule shown in FIG. 5a and described above. Accordingly, for brevity and simplicity, components which are exactly the same as that of the second preferred embodiment and the carpule of FIG. 5a are given exactly the same reference numerals on FIGS. 6, 7, 8 and 9 as the corresponding components were given on FIGS. 4 and 5a. Similarly, for the sake of brevity, a detailed description of each of these components will not be presented again but may be obtained by reference to the above description.

The primary differences between the embodiment shown in FIGS. 6-9 and the embodiment shown in FIG. 4 lies in the manner in which the carpule 302 is secured to the forward or proximal end of the housing 220 and the manner in which the needle is secured to the remainer of the syringe 50. In the embodiment shown in FIGS. 6-9 no connector component 204 or connecting tube 202 of the type employed in the embodiment of FIG. 4 are utilized. Instead, the delivery needle 800 is secured directly to the carpule 302 in a manner which will hereinafter be described in greater detail.

Figure 6:
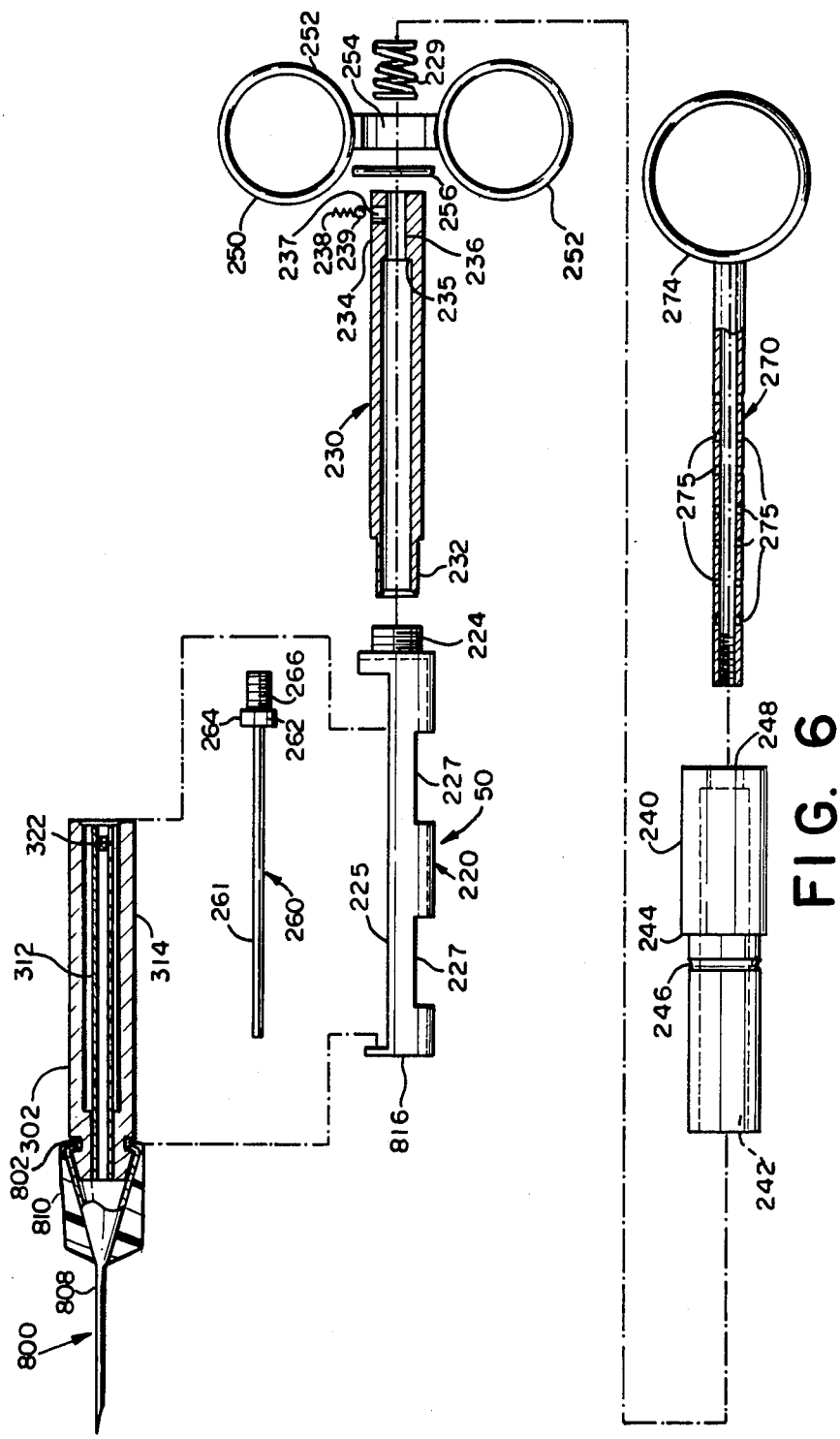
FIG. 6 is an exploded partially sectioned side elevational view of a third preferred embodiment of a syringe in accordance with the present invention.
Figure 8:
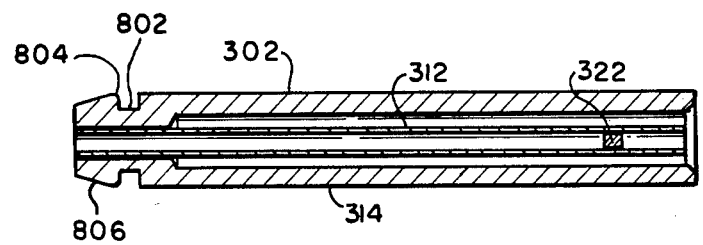
FIG. 8 is an enlarged sectional view of the carpule and portion of the syringe of FIG. 6.
Figure 9:
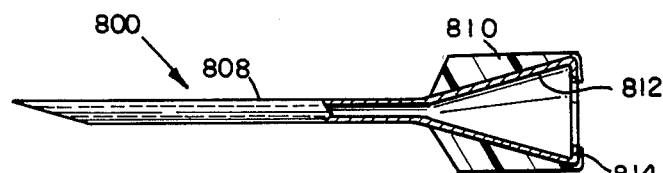
FIG. 9 is an enlarged sectional view of the needle portion of the syringe of FIG. 6.

Referring now to FIGS. 8 and 9, there is shown, in greater detail, an enlarged sectional view of the carpule 302 and needle 800 portions of the syringe 50 of FIG. 6. The carpule 302 is similar to the carpule shown in FIG. 5a and includes an interior tube or bore 312 preferably manufactured from the stainless steel tubing or a material having similar properties which contains the fluid to be delivered. A polytetrafluoroethylene plug 322 cooperates with the plunger member 260 (FIG. 6) to move along the carpule tube 312 for delivering the fluid within the carpule 302 in substantially the same manner as the carpule of FIG. 5a.

The forward or proximal end of the carpule 302 includes a generally annular groove 802 extending around the radial circumference. For purposes which will hereinafter become apparent, the edge 804 of the groove 802 proximate the forward end of the carpule 302 is beveled or rounded. The portion 806 of the carpule 302 extending forward (toward the left one viewing FIG. 8) from the groove 802 is beveled or inwardly tapered, the taper being preferably a luer lock taper.

Correspondingly, the needle 800 is of a type well known in the art and is comprised of a special extra thick flanged generally tubular delivery portion 808 which is supported within a generally cylindrical connector member 810. The rearward end of the connector member 810 includes an interior beveled or tapered portion 812 which is sized and tapered to complement the tapered portion 806 on the forward end of the carpule 302. Thus, when the needle 800 and the carpule are joined together as shown in FIG. 6 the tapered portions 806 and 812 complement each other to provide a fluid type seal between the needle 800 and the carpule 302.

The rearward end of the connector member 810 further includes an annual flange member 814 (see FIGS. 6 and 9). When the needle 800 is installed on the carpule 302 the annular flange member 814 is formed during assembly when the end of the needle connector member 810 is bent or peened inwardly and into the groove 802 as shown in FIG. 6. For clarity, FIG. 9 shows the annular flange member 814 in the position it assumes after installation on the carpule 302. The combination of the engagement of the two tapered portions 806 and 812 and the engagement of the flange member 814 with the groove 802 firmly secures the needle 800 to the forward end of the carpule 302.

Figure 7:
FIG. 7 is a fragmentary end view of the housing of the syringe of FIG. 6.

Referring now to FIGS. 6 and 7, it can be seen that the proximal or forward end of the cylindrical housing 220 includes a generally arcuate member 816 which comprises the forwardmost end of the housing 220. The arcuate member 816 is adapted to receive and engage the groove 802 on the forward end of the carpule 302 when the carpule is installed within the housing 220. The outer circumference of the arcuate member 816 is the same or slightly greater than the outer diameter of the carpule 302 while the inner diameter of the arcuate member 816 is the same or slightly greater than the diameter of the portion of the carpule surrounded by the groove 802. The carpule 302 is installed within the housing by aligning the carpule 302 with the housing opening 225 and pushing the carpule 302 and housing 220 together. When the groove 802 initially engages the arcuate member 816 the unattached ends of the arcuate member 816 are spread apart to afford entry of the groove 802 and then spring back toward each other to hold the carpule 302 securely in place within the housing 220. The axial length of the groove 802 is sufficient to accommodate both the annular flange member 814 and the arcuate member 816. Removal of the carpule 302 from the housing 220 is accomplished by reversing the assembly process.

Operation of the syringe shown in FIG. 6 is exactly the same as that described above in connection with the syringe shown in FIG. 4. Therefore, specific details of the operation will not be repeated.

It will be recognized by those skilled in the art that changes may be made to the above-described embodiments of the invention without departing from the broad inventive concepts thereof. For example, the detent feature illustrated in connection with the carpule syringe 50 may also be used with the direct fill syringe 20. It is understood, therefore, that this invention is not limited to the particular embodiments disclosed, but is intended to cover any modifications which are in the scope and spirit of the invention as defined by the pendent claims.

We claim:

1. A carpule system for the microadministration of viscous fluid including a carpule syringe comprising
  a stainless steel delivery needle having an interior diameter in the range of from about 0.004 inches to about 0.007 inches;
  a generally cylindrical fluid containing carpule having a bore with a cross-sectional area which is about 100 to 400 times greater than the cross-sectional area of the bore of the delivery needle and a movable plug sealing the fluid within the carpule, the needle being secured to one end of the carpule;
  a generally cylindrical housing member having openings at each end and adapted to receive the carpule, the housing member having means on one end for retaining the one end of the carpule;
  an adapter member secured to the other end of the housing member to secure the other end of the carpule within the housing member;
  adapter retention means for securing the adapter member to the other end of the housing member;
  a plunger adapted to axially displace the carpule plug within the carpule bore for delivery of the fluid;
  gripper means including finger grip means secured to at least one of the housing member, adapter member and adapter retention means, and thumb grip means secured to the plunger, the gripper means for facilitating movement of the plunger relative to the carpule.

2. A carpule system according to claim 1 wherein the plunger comprises a rod having spaced, circumferential grooves adapted to be engaged by a detent means within the adapter member when the plunger is displaced axially.

3. A carpule system according to claim 1 wherein the other end of the carpule is sealed with a plug member which is chemically inert with respect to the fluid and which is adapted to slidingly engage the interior surface of the carpule and seal the fluid within the carpule as the plug is axially displaced.

4. A carpule system according to claim 1 wherein the means for retaining the one end of the carpule received within the housing comprises a generally arcuate member on the proximal end of the housing, the arcuate member being adapted to grip and retain the carpule.

5. A carpule system according to claim 4 wherein the carpule includes a generally annular groove on the one end, the groove being adapted to be engaged by the arcuate member.

6. A carpule system according to claim 1 wherein the one end of the carpule includes a tapered portion and the needle includes a connector having a complementary tapered portion, the tapered portion of the carpule being adapted to sealingly engage the tapered portion on the needle connector for securing the needle to the carpule and providing a fluid tight seal.

7. A carpule system according to claim 6 wherein the carpule further comprises a generally annular groove extending around the circumference proximate the one end and wherein the needle connector further includes a generally annular flange member, the flange member of the needle connector being adapted to engage the carpule groove to secure the needle to the carpule.

8. A carpule system for the microadministration of viscous fluid including a carpule syringe comprising
    a stainless steel delivery needle having an interior diameter in the range of from about 0.004 inches to about 0.007 inches;
    a generally cylindrical housing member having openings at each end and adapted to receive a generally cylindrical fluid containing sealed carpule having a bore with a cross-sectional area which is about 100 to 400 times greater than the cross sectional area of the bore of the delivery needle, and a movable plug sealing the fluid with the carpule, the housing member having means on one end for retaining one end of the carpule, the needle being secured to the one end of the carpule;
    an adapter member secured to the other end of the housing member to secure the other end of the carpule within the housing member;
    adapter retention means for securing the adapter member to the other end of the housing member;
    a plunger adapted to axially displace the carpule plug within the carpule bore for delivery of the fluid;
    gripper means including finger grip means secured to at least one of the housing member, adapter member and adapter retention means, and thumb grip means secured to the plunger, the gripper means for facilitating movement of the plunger relative to the carpule.

9. A carpule system according to claim 8 wherein the other end of the carpule is sealed with a plug member which is chemically inert with respect to the fluid and which is adapted to slidingly engage the interior surface of the carpule and seal the fluid within the carpule as the plug is axially displaced.

10. A carpule system according to claim 9 wherein the carpule has a glass body.

11. A carpule system according to claim 9 wherein the carpule has a stainless steel interior tube containing the viscous fluid.

12. A carpule system according to claim 8 wherein the means for retaining the one end of the carpule received within the housing comprises a generally arcuate member on the proximal end of the housing, the arcuate member being adapted to grip and retain the carpule.

13. A carpule system according to claim 12 wherein the carpule includes a generally annular groove on the one end, the groove being adapted to be engaged by the arcuate member.

14. A carpule system according to claim 8 wherein the one end of the carpule includes a tapered portion and the needle includes a connector having a complementary tapered portion, the tapered portion of the carpule being adapted to sealingly engage the tapered portion on the needle connector for securing the needle to the carpule and providing a fluid tight seal.

15. A carpule system according to claim 14 wherein the carpule further comprises a generally annular groove extending around the circumference proximate the one end and wherein the needle connector further includes a generally annular flange member, the flange member of the needle connector being adapted to engage the carpule groove to secure the needle to the carpule.

* * * * *